United States Patent
Ridgway

(10) Patent No.: US 9,938,348 B2
(45) Date of Patent: Apr. 10, 2018

(54) STIMULATION VIA TLR4/MD-2 TO REVERSE TYPE 1 DIABETES

(71) Applicant: University of Cincinnati, Cincinnati, OH (US)

(72) Inventor: William Ridgway, Terrace Park, OH (US)

(73) Assignee: University of Cincinnati, Cincinnati, OH (US)

(*) Notice: Subject to any disclaimer, the term of this patent is extended or adjusted under 35 U.S.C. 154(b) by 0 days.

(21) Appl. No.: 15/302,772

(22) PCT Filed: Apr. 17, 2015

(86) PCT No.: PCT/US2015/026444
§ 371 (c)(1),
(2) Date: Oct. 7, 2016

(87) PCT Pub. No.: WO2015/161234
PCT Pub. Date: Oct. 22, 2015

(65) Prior Publication Data
US 2017/0029523 A1    Feb. 2, 2017

Related U.S. Application Data

(60) Provisional application No. 61/981,256, filed on Apr. 18, 2014.

(51) Int. Cl.
| | | |
|---|---|---|
| A61K 39/395 | (2006.01) | |
| C07K 16/28 | (2006.01) | |
| A61K 31/7016 | (2006.01) | |
| C07K 14/705 | (2006.01) | |
| C07K 14/71 | (2006.01) | |
| A61K 39/00 | (2006.01) | |

(52) U.S. Cl.
CPC ...... C07K 16/2896 (2013.01); A61K 31/7016 (2013.01); A61K 39/3955 (2013.01); A61K 2039/505 (2013.01); C07K 16/28 (2013.01); C07K 2317/75 (2013.01)

(58) Field of Classification Search
CPC ........ A61K 38/191; A61K 2039/55572; A61K 2039/505; A61K 38/17; A61K 38/177; A61K 38/18; A61K 38/19; A61K 39/3955; A61K 38/1709; A61K 39/395; C07K 2317/75; C07K 16/18; C07K 16/2896; C07K 14/435; C07K 14/475; C07K 14/52; C07K 14/705; C07K 16/22; C07K 16/24; C07K 16/28; C07K 16/2863; C07K 16/2866
See application file for complete search history.

(56) References Cited

U.S. PATENT DOCUMENTS 5,292,641 A     3/1994  Pouletty
7,312,320 B2 *  12/2007  Elson ................... C07K 16/18
                                              424/130.1

OTHER PUBLICATIONS

Aumeunier et al. Systemic toll-like receptor stimulation suppresses experimental allergic asthma and autoimmune diabetes in NOD mice. PLoS One 5(7): e11484, 2010 (14 pages).*
Bednar et al. Reversal of new-onset type I diabetes with an agonistic TLR4/MD-2 monoclonal antibody. Diabetes 64: 3614-3626, 2015.*
Caramalho et al. Regulatory T cells contribute to diabetes protection in lipopolysaccharide-treated non-obese diabetic mice. Scand J Immunol 74(6): 585-595, 2011.*
Hennessy et al. Targeting Toll-like receptors: emerging therapeutics? Nat Rev Drug Discovery 9(4): 293-307, 2010.*
Wang et al. TLR4 homotolerance and regulatory T cells are involved in the protection against insulitis in non-obese diabetic mice by lipopolysaccharide. Acta Pharmacol Sinica 34(Suppl 1): 91, 2013.*
Akashi-Takamura eta l. Agonistic antibody to TLR4/MD-2 protects mice from acute lethal hepatitis induced by TNF-alpha. J Immunol 176L 4244-4251, 2006.*
Alyanakian, M-A., et al., "Transforming Growth Factor-β and Natural Killer T-Cells Are Involved in the Protective Effect of a Bacterial Extract on Type 1 Diabetes," Diabetes 55:179-185 (2006).
Atkinson, M. A., Eisenbarth, G. S. & Michels, A. W., "Type 1 diabetes," Lancet 383, 69-82, doi:S0140-6736(13)60591-7 [pii] 10.1016/S0140-6736(13)60591-7 (2014).
Bach, J. F. & Chatenoud, L., "The hygiene hypothesis: an explanation for the increased frequency of insulin-dependent diabetes," Cold Spring Harb Perspect Med 2, a007799, doi:10.1101/cshperspect.a007799 a007799 [pii] (2012).
Bahrun, U. et al., "Preparation and characterization of agonistic monoclonal antibodies against Toll-like receptor 4-MD-2 complex," Hybridoma (Larchmt) 26, 393-399, doi:10.1089/hyb.2007.0523 (2007). Abstract only.
Bednar, K., et al., "Toll-like receptor 4 agonistic monoclonal antibody reverses new onset type 1 diabetes (BA12P.106)," J Immunol, 192(1) Suppl. 176.7, May 1, 2014, 2 pgs.
Bour-Jordan, H. et al., "Costimulation controls diabetes by altering the balance of pathogenic and regulatory T cells," J Clin Invest 114, 979-987, doi:10.1172/JCI20483 (2004).
Chong, A. S. et al., "Reversal of diabetes in non-obese diabetic mice without spleen cell-derived beta cell regeneration," Science 311, 1774-1775, doi:311/5768/1774 [pii] 10.1126/science.1123510 (2006).
Culina, S., Boitard, C. & Mallone, R. "Antigen-based immune therapeutics for type 1 diabetes: magic bullets or ordinary blanks?" Clin Dev Immunol 2011, 286248, doi:10.1155/2011/286248 (2011).
Dong, B. et al. "TLR4 regulates cardiac lipid accumulation and diabetic heart disease in the nonobese diabetic mouse model of type 1 diabetes," Am J Physiol Heart Circ Physiol 303, H732-742, doi:10.1152/ajpheart.00948.2011 (2012).
(Continued)

*Primary Examiner* — Bridget E Bunner
(74) *Attorney, Agent, or Firm* — Frost Brown Todd LLC

(57) ABSTRACT

Disclosed are methods and compositions for treating Type I diabetes in a subject. Agents selected from a TLR4 agonist, a TLR4/MD-2 agonist, or a combination thereof may be used in the disclosed methods and compositions. Also disclosed are methods of restoring adaptive immune T cell tolerance, treating pernicious insulitis, improving immune tolerance, and treating autoimmune diseases using the disclosed methods and compositions.

4 Claims, 13 Drawing Sheets

(56) References Cited

OTHER PUBLICATIONS

Gale, E. A. "The rise of childhood type 1 diabetes in the 20th century," Diabetes 51, 3353-3361 (2002).
Gardner, S. G., Bingley, P. J., Sawtell, P. A., Weeks, S. & Gale, E. A. "Rising incidence of insulin dependent diabetes in children aged under 5 years in the Oxford region: time trend analysis," The Bart's-Oxford Study Group. BMJ 315, 713-717 (1997).
Gulden, E. et al. "Toll-like receptor 4 deficiency accelerates the development of insulin-deficient diabetes in non-obese diabetic mice," PLoS One 8, e75385, doi:10.1371/journal.pone.0075385 (2013).
Long, A. E., Gillespie, K. M., Rokni, S., Bingley, P. J. & Williams, A. J. "Rising incidence of type 1 diabetes is associated with altered immunophenotype at diagnosis," Diabetes 61, 683-686, doi:db11-0962 [pii] 10.2337/db11-0962 (2012).
Mabley, J.G., et al., "The novel inosine analogue, INO-2002, protects against diabetes development in multiple low-dose streptozotocin and non-obese diabetic mouse models of type 1 diabetes," J Endocrinology 198, 581-589, (2008).
Madonna, G. S., Peterson, J. E., Ribi, E. E. & Vogel, S. N. "Early-phase endotoxin tolerance: induction by a detoxified lipid A derivative, monophosphoryl lipid A," Infect Immun 52, 6-11 (1986).
Matsushita, H. et al. "Endotoxin tolerance attenuates airway allergic-inflammation in model mice by suppression of the T-cell stimulatory effect of dendritic cells," Int Immunol 22, 739-747, doi:dxq062 [pii] 10.1093/intimm/dxq062 (2010).
Michaud, J. P. et al. "Toll-like receptor 4 stimulation with the detoxified ligand monophosphoryl lipid A improves Alzheimer's disease-related pathology," Proc Natl Acad Sci U S A 110, 1941-1946, doi:1215165110 [pii] 10.1073/pnas.1215165110 (2013).
Nikolic, T., Geutskens, S. B., van Rooijen, N., Drexhage, H. A. & Leenen, P. J. "Dendritic cells and macrophages are essential for the retention of lymphocytes in (peri)-insulitis of the nonobese diabetic mouse: a phagocyte depletion study," Lab Invest 85, 487-501, doi:3700238 [pii] 10.1038/labinvest.3700238 (2005).
Nishio, J. et al. "Islet recovery and reversal of murine type 1 diabetes in the absence of any infused spleen cell contribution," Science 311, 1775-1778, doi:311/5768/1775 [pii] 10.1126/science.1124004 (2006).

Ohta, S. et al. "Induction of Long-Term Lipopolysaccharide Tolerance by an Agonistic Monoclonal Antibody to the Toll-Like Receptor 4/MD-2 Complex," Clin Vaccine Immunol 13, 1131-1136, doi:13/10/1131 [pii] 10.1128/CVI.00173-06 (2006).
Okubo, Y. et al. "Hyperplastic islets observed in "reversed" NOD mice treated without hematopoietic cells," Diabetes Res Clin Pract 79, 18-23, doi:S0168-8227(07)00428-7 [pii] 10.1016/j.diabres.2007.08.020 (2008).
Onkamo, P., Vaananen, S., Karvonen, M. & Tuomilehto, J. "Worldwide increase in incidence of Type I diabetes—the analysis of the data on published incidence trends," Diabetologia 42, 1395-1403, doi:10.1007/s001250051309 (1999).
Patterson, C. C., Dahlquist, G. G., Gyurus, E., Green, A. & Soltesz, G. "Incidence trends for childhood type 1 diabetes in Europe during 1989-2003 and predicted new cases 2005-20: a multicentre prospective registration study," Lancet 373, 2027-2033, doi:S0140-6736(09)60568-7 [pii] 10.1016/S0140-6736(09)60568-7 (2009).
Serreze, D. V., Gaedeke, J. W. & Leiter, E. H. "Hematopoietic stem-cell defects underlying abnormal macrophage development and maturation in NOD/Lt mice: defective regulation of cytokine receptors and protein kinase C," Proc Natl Acad Sci U S A 90, 9625-9629 (1993).
Sreenan, S. et al. "Increased beta-cell proliferation and reduced mass before diabetes onset in the nonobese diabetic mouse," Diabetes 48, 989-996 (1999).
Vacchelli, E. et al. "Trial watch: FDA-approved Toll-like receptor agonists for cancer therapy," Oncoimmunology 1, 894-907, doi:10.4161/onci.20931 2012ONCOIMM0177 [pii] (2012).
Weaver, D. J., Jr. et al. "Dendritic cells from nonobese diabetic mice exhibit a defect in NF-kappa B regulation due to a hyperactive I kappa B kinase," J Immunol 167, 1461-1468 (2001).
International Search Report and Written Opinion dated Jul. 22, 2015 for Application No. PCT/US2015/026444, 10 pgs.
International Preliminary Report on Patentability dated Oct. 18, 2016 for Application No. PCT/US2015/026444, 8 pgs.
Buscaroli, A., et al., "Application of Prastat ELISA in the determination of anti-HLA specificity for immunized patients awaiting kidney transplant: five years' experience", Transpl Int, 2000, 13(Suppl 1):S99-S105, 7 pgs.

* cited by examiner

STIMULATION VIA TLR4/MD-2 TO REVERSE TYPE 1 DIABETES

This application is a U.S. National Stage application under 35 USC § 371 which claims priority to and benefit of PCT/US2015/026444, filed Apr. 17, 2015, which in turn claims priority to and benefit of U.S. Provisional Application No. 61/981,256, titled "Stimulation via TLR4/MD-2 To Reverse Type 1 Diabetes," filed Apr. 18, 2014, the contents of each are incorporated herein in their entirety for all purposes.

BACKGROUND

The incidence of Type 1 diabetes ("T1D") has risen rapidly worldwide since the mid-20th century, increasing by 3-4% per annum in Europe and America (1-5). T1D is currently an incurable disease, characterized by an acute clinical phase, reflecting progressive autoimmune destruction of insulin-producing pancreatic beta cells. There is no effective treatment to reverse new onset T1D, despite a vast increase in knowledge of its immunogenetic basis. (6) Despite the fact that autoreactive T cells undeniably mediate tissue destruction and cause T1D in mice and humans, clinical trials testing the effect of immunotherapy directed toward specific autoantigens have been disappointing (1). Culina et al. document at least 36 clinical trials of various peptides including GAD and insulin in human T1D (2). These trials have essentially failed to achieve stabilization or reversal of diabetes, indicating the need to keep investigating new therapeutic approaches and combination therapies (3).

The instant disclosure seeks to address one or more of the aforementioned needs in the art, including improved treatments for T1D and autoimmune diseases.

BRIEF SUMMARY

Disclosed are methods and compositions for treating Type I diabetes in a subject. Agents selected from a TLR4 agonist, a TLR4/MD-2 agonist, or a combination thereof may be used in the disclosed methods and compositions. Also disclosed are methods of restoring adaptive immune T cell tolerance, treating pernicious insulitis, improving immune tolerance, and treating autoimmune diseases using the disclosed methods and compositions.

BRIEF DESCRIPTION OF THE DRAWING

FIG. 1A: 6-8 week old female NOD mice were treated three times one week apart with UT15-Ab (n=13), UT18-Ab (n=13) or untreated (n=17), and diabetes assessed for 200 days. P=<0.005, and *P=<0.0001, Log-Rank test. FIG. 1B: Insulitis severity scores: at the time of diabetes onset or after 200 days the pancreas was scored for insulitis (see methods); the percentage of each stage of insulitis is shown. FIG. 1C: Representative islets from each group are shown. (FIG. 1D, FIG. 1E) Groups of female NOD mice were treated with UT18-Ab, UT15-Ab or PBS and the indicated splenic cell subsets were assessed by FACS at 24 hours (FIG. 1D) or 28 days(e) (n=2 PBS, n=5 UT15-Ab, n=5 UT18-Ab). UT18, but not UT15, rapidly induced expansion of macrophages, dendritic cells, and B cells, but had no effects on T cell numbers or proliferation. P=<0.05, unpaired T test. FIG. 1F: NOD mice were injected with PBS (n=2), UT15-Ab (n=4) or UT18-Ab (n=4) once a week for two weeks. 24 hours after the final treatment splenocytes were removed and the cells were assessed numbers of each cell subset. FIG. 1G: UT18-Ab does not cause CD4+ T cell proliferation. Purified CD4+ cells treated with UT18-Ab (n=4) or UT15-Ab (n=4) proliferate no differently than unstimulated controls (N=4), compared to CD3/CD28 stimulation (n=4). FIG. 1H: UT18 treatment results in significant increases in the number of T regulatory cells. P<0.01 by unpaired T test.

FIG. 2A-2D: Female NOD mice were randomly assigned to UT15-Ab or UT18-Ab groups and then monitored until the earliest signs of T1D (polyuria); at this time the average BG was 208.3±16.1 mg/dL. Mice were then treated twice, one week apart, with either UT15-Ab (n=12) or UT18-Ab (n=21). Detailed time course of blood glucose with UT15-Ab treatment (FIG. 2A) or UT18-Ab (FIGS. 2B,2C,2D). Mice were either treated twice with UT18 (FIG. 2C, upper right panel, n=11), or retreated with UT18 after the initial 2 treatments, (FIG. 2D, lower right panel, n=10) if the BG rose above 200 mg/dl after the initial two treatments. Red time point indicates time of first retreatment (FIG. 2D). FIG. 2E: UT18 significantly reverses T1D compared to UT15 (p<0.001, unpaired T test). FIG. 2F: UT18-Ab reverses T1D induced weight loss. Blood glucose and weight were monitored weekly in female NOD mice. Mice (n=6 both groups) were treated with UT18-Ab or UT15-Ab starting at time point 3. Time intervals equal one week except the last interval which varied from 3-7 days. *P=<0.01, unpaired T test. FIG. 2G: UT18-Ab improves insulitis in new onset T1D. Pancreatic insulitis was assessed by a blinded observer in 5 groups: DM-mice (n=7, 6 week old female NOD mice), "BG200" mice (at onset of T1D, n=5, mice at a blood glucose of ~200 mg/dL when treatment is initiated)), "DM (+)" (n=10, endstage diabetes (blood glucose >500 mg/dL), UT15-Ab treated mice (n=9, the first 6 cohorts of mice from FIG. 2A above) and UT18-Ab treated mice (n=13, the first 6 cohorts of mice from FIG. 2B above), **P=<0.008, Mann-Whitney test.

FIG. 3A: Percentage of islets at each stage of insulitis (scored blindly) in five groups: "DM(−)" (n=7, 6 week old female NOD mice), "BG200" (n=5, mice at a blood glucose of ~200 mg/dL when treatment is initiated), "DM(+)" (n=10, endstage diabetes (blood glucose >500 mg/dL)), "UT15-Ab" (n=9) and "UT18-Ab" (n=13). FIG. 3B: Pancreatic sections from mice in each group were stained for insulin and glucagon by immunohisotochemistry; representative islets from each group are shown. FIG. 3C: Total insulin positive area per section, quantified using ImageJ analysis (see methods). P=<0.005, and *P=<0.0001, unpaired T test FIG. 3D: Total number of insulin positive islets per section. *P=<0.02, P=<0.003, and *P=<0.0001, unpaired T test. FIG. 3E: Increased beta cell insulin positive area per insulin positive islet in UT18-mAb treated mice *P=<0.02 and **P=<0.001 unpaired T test.

FIG. 4A: 6 week old female NOD.scid mice were treated three times one week apart with either UT18-Ab (n=15), or untreated (unTx, n=10). $2\times10^6$ CD4$^+$ and $1\times10^6$ CD8$^+$ T-cells from pre-diabetic NOD mice (6 weeks) were transferred into the NOD.scid recipients and diabetes onset was monitored for 75 days. FIG. 4B: Individual islet histological scores are shown for untreated control (n=10), and UT18-Ab treated (n=11) NOD.scid T cell recipients. Representative islet histology is shown for each group. FIG. 4C: Total splenic Tregs (CD4$^+$Foxp3$^+$) were assessed at time of overt diabetes or at 75 days after treatment from unTx (n=8), or UT18-Ab treated (n=7) NOD.scid recipient mice. *P<0.04, unpaired T test. Representative FACs plots are shown.

DETAILED DESCRIPTION

Figure 1A:
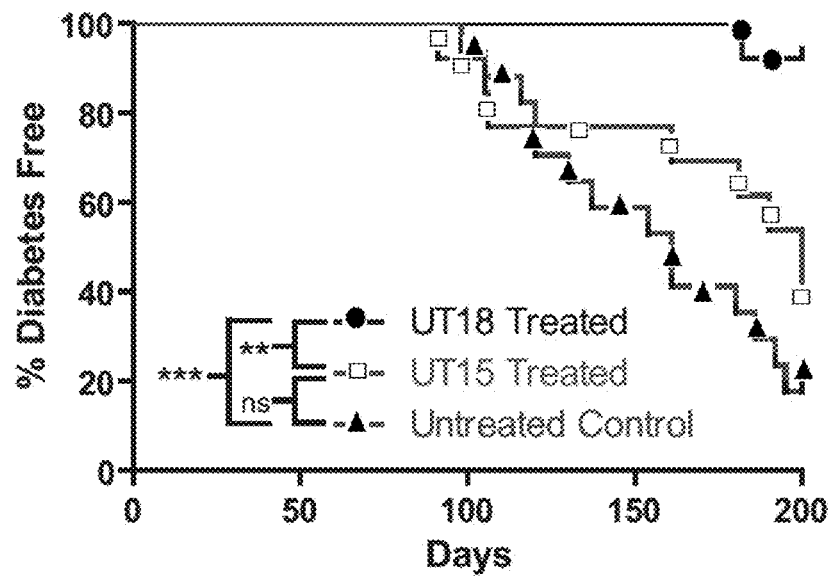
FIGS. 1A-1H demonstrate that UT18-Ab prevents T1D and reduces insulitis.
Figure 1B:
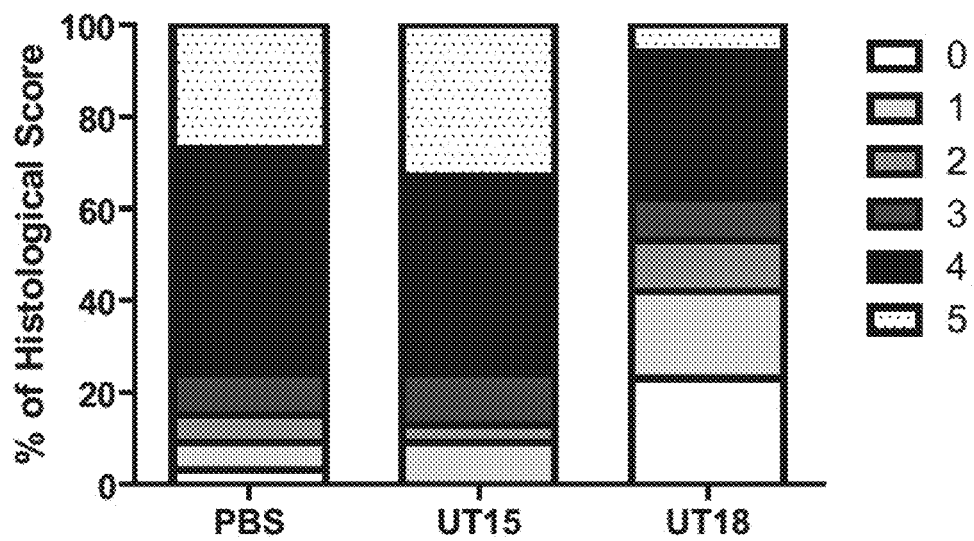
Figure 1C:
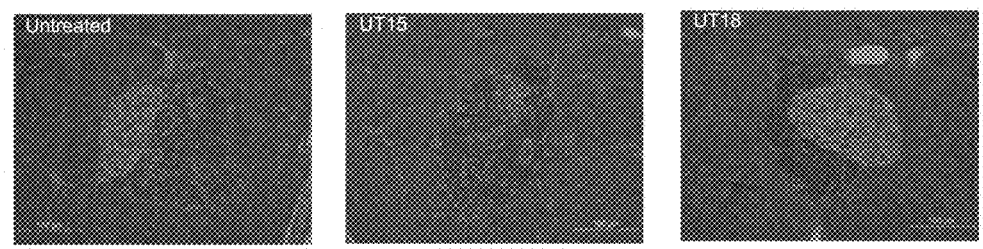
Figure 1D:
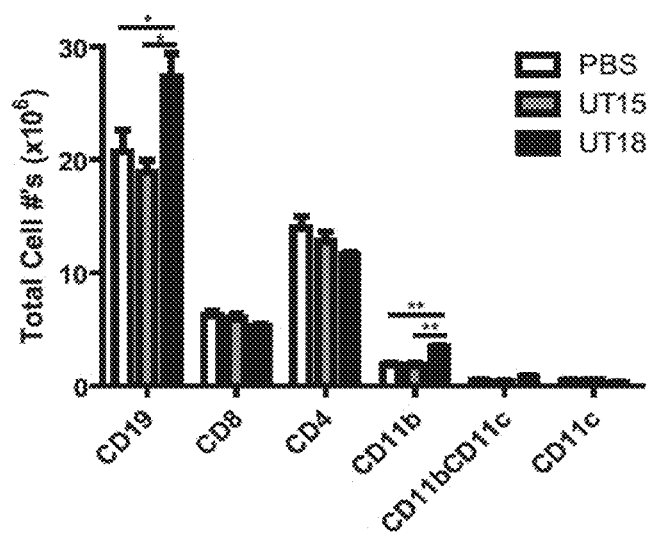
Figure 1E:
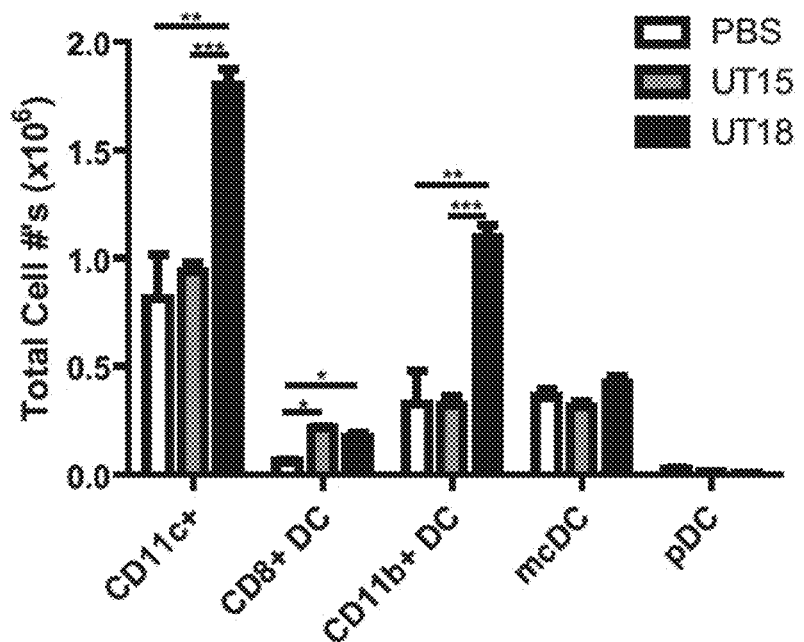
Figure 1F:
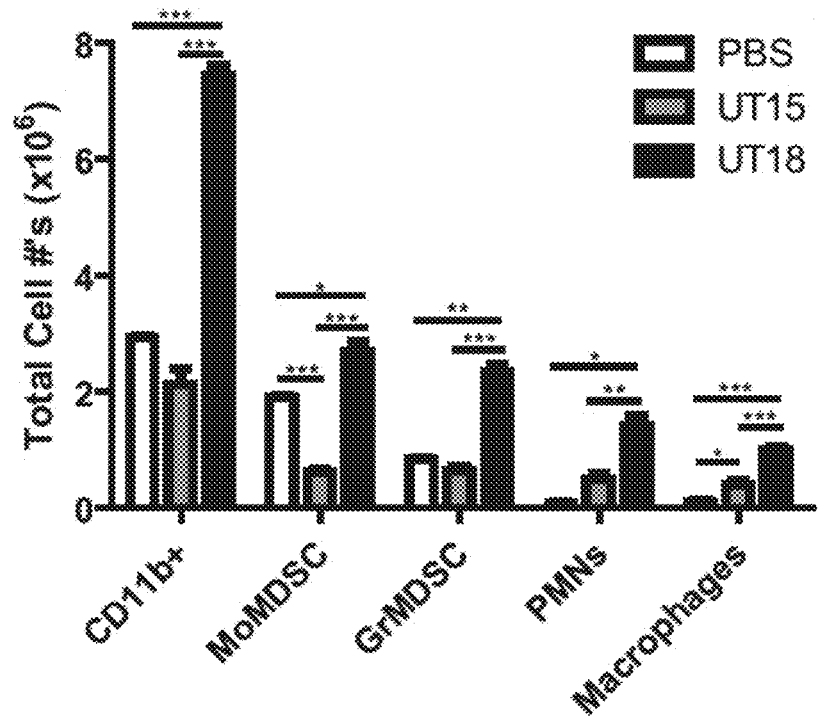
Figure 1G:
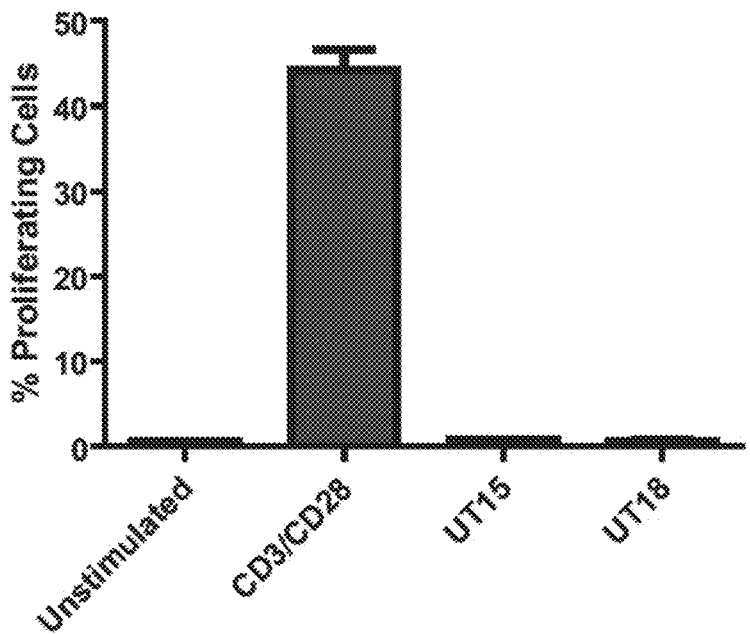
Figure 1H:
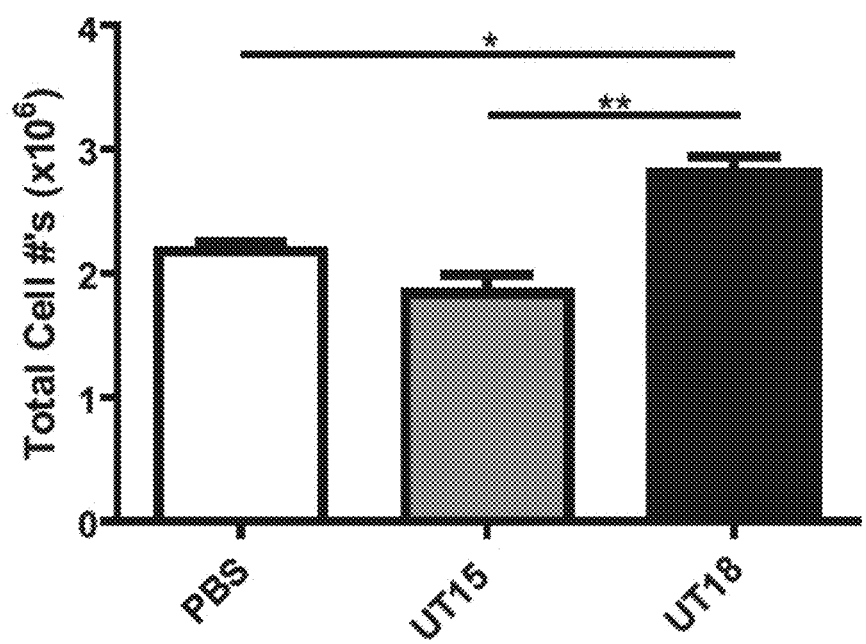

Applicant has identified a new pathway for reversing Type 1 Diabetes ("T1D"), offering new therapeutic approaches to this difficult disease. Methods of selectively stimulating an arm of the innate immune system that may ultimately be used in a "combination" therapy approach as routinely used to treat other autoimmune diseases such as rheumatoid arthritis, are disclosed. In particular, Applicant has found that an agonistic monoclonal antibody to TLR4/MD-2 (TLR4-Ab) may be useful for reversing new onset diabetes.

Toll-Like receptors (TLRs) are innate pattern recognition receptors that are involved in the host defense against multiple pathogens. The TLR4 receptor must be in complex with MD-2 in order to signal in response to its ligand, lipopolysaccharide (LPS), an integral component of gram negative bacteria. The TLR4 receptor is stimulated by Lipopolysaccharide (LPS), which is an integral component of gram negative bacterial cell wall. Stimulation through TLR4 alone is insufficient; MD2 must be bound to TLR4 for effective signaling. LPS also requires CD14 and serum LPS binding protein (LBP) to transport it to the receptor complex of TLR4/MD2. One unique cellular effect of LPS is "endotoxin tolerance", wherein lower doses of LPS induce tolerance rather than activation of immune cells (17, 18). TLR4/MD-2 signaling is mediated through two main adaptor molecules, MyD88 and Trif, and produces inflammatory modulators such as TNF-α, IFN-β and IL-10, TLR4 expressing cells can also undergo endotoxin tolerance. These endotoxin tolerized cells have a decreased inflammatory response to re-challenge (19). Endotoxin tolerance is critical for hepatic immunity; the liver is exposed to low dose LPS from the gut and LPS tolerance mediated through APCs creates a "tolerogenic" hepatic immune environment (20).

Applicant has discovered that the adaptive immune response to self can be re-tolerized by stimulation of innate immunity via TLR4/MD-2. In other words, Applicant has found that T cells from formerly diabetic mice treated with agonist TLR4/MD-2 specific monocolonal antibodies (designated "UT18") can no longer transfer disease. This is a surprising result, as there is no evidence to date that UT18 acts directly on T cells, and the mechanisms of how tolerance is restored are of great significance. Applicant's discovery is further significant because some TLR4 agonists (e.g. Monophosphoryl lipid A (MPLA) (4, 5)) are FDA approved in humans, and new agents are being developed, such that a pathway to human application of these studies already exists and can be used to eventually apply this approach to the treatment of human disease.

There are known abnormalities in nonobese diabetic ("NOD") innate immunity, including in macrophages (Sereze and Leiter showed that NOD macrophages were developmentally defective (6) and dendritic cells (DCs; Tisch et al. showed an intrinsic signaling defect in NOD DCs (7)). Macrophages and DCs are amongst the earliest invading cells in insulitis, are needed to maintain disease pathogenesis (8), and produce pro-inflammatory TNF-α (9). Modulating innate immunity via macrophages/DCs affects critical co-stimulation of T cells, and can alter the balance of T regulatory (Treg) and T effector (Teff) mechanisms (10). Depleting DCs (but not macrophages) can prevent diabetes; moreover a subset of "merocytic" DC's promote NOD diabetes (11, 12). However, the therapeutic targeting of antigen specific T cells (directed to GAD, insulin etc) has not worked, without explanation. Without intending to be limited by theory, Applicant theorizes that one possibility is that underlying innate immune defects promote the establishment and persistence of antigen specific adaptive immune abnormalities. Eliminating one set of antigen specific T cells may simply allow another set of T cells to arise (determinant spreading).

In one aspect, the instant compositions and methods relate to a novel approach of resetting or retuning an immune response globally via stimulating a specific pathway of innate immunity to treat T1D and related disorders such as autoimmune diseases. This approach is different from current immunosuppressive approaches (e.g. anti-TNF therapy or methotrexate) in autoimmune diseases such as rheumatoid arthritis (RA) or multiple sclerosis (MS). The broadest theoretical basis for therapeutic stimulation of innate immunity is the "hygiene hypothesis", which suggests that the incidence of autoimmunity is increasing due to decreased immune stimulation (via exposure to infectious agents) in childhood. This has been proposed as the basis of many diseases including T1D (13). Bach and Chatenoud showed that "dirty" animal rooms decreased NOD diabetes and that diabetes incidence can be increased by raising the mice in cleaner cages (13). Many infectious diseases and inflammatory agents can prevent NOD diabetes, (13-16) but none of these has so far been shown to reverse it.

In one aspect, a method of treating Type I diabetes in a subject, comprising the step of administering an agent selected from a TLR4 agonist, a TLR4/MD-2 agonist, or a combination thereof is disclosed. The Type I diabetes may be, in one aspect, new onset diabetes.

In one aspect, the TLR4/MD-2 agonist may be a TLR4/MD-2 specific antibody or an antigen-binding fragment. In one aspect, the agonist may be a polyclonal antibody, a monoclonal antibody, or combinations thereof. In one aspect, the antibody is a monoclonal antibody.

In one aspect, the TLR4/MD-2 agonist is administered in an amount sufficient to activate TLR4/MD-2.

In one aspect, the agent may comprise a TLR4 agonist. The TLR4 agonist may comprise monophosphoryl lipid A (MPLA).

In one aspect, a method of treating an autoimmune disease in a subject, comprising the step of stimulating TLR4/MD-2, is disclosed. The autoimmune disease may be selected, for example, from rheumatoid arthritis, multiple sclerosis, and Type I diabetes. The stimulation step may be carried out by administration of an agent selected from a TLR4 agonist, a TLR4/MD-2 agonist, or a combination thereof. In one aspect, the stimulation step may be carried out by administration of a composition comprising monophosphoryl lipid A (MPLA) and a pharmaceutically acceptable excipient. In a further aspect, the stimulation step may be carried out by administration of a TLR4/ND-2 specific antibody or an antigen-binding fragment thereof. In one aspect, the antibody may be monoclonal.

In one aspect, a method of stimulating innate immunity in a subject, comprising the step of stimulating TLR4/MD-2 is disclosed.

In one aspect, a method of restoring adaptive immune T cell tolerance in a subject in need thereof, comprising stimulating TLR4/MD-2, is disclosed.

In one aspect, a method of treating pernicious insulitis, comprising the step of stimulating TLR4/MD-2, wherein said stimulating step converts said pernicious insulitis to benign insulitis is disclosed.

In one aspect, a method of improving immune tolerance comprising administering to the subject an effective TLR4/MD-2 activating amount of a TLR4/ND-2 specific antibody or an antigen-binding fragment thereof is disclosed.

Compositions for the treatment of one or more aforementioned disease states are also disclosed. Such compositions may comprise one or more of the agents disclosed herein, and a pharmaceutically acceptable excipient. The disclosed agents may also be combined with other agents known and used for the treatment of one or more disclosed disease states and prepared as a combination therapy. Such formulations will generally employ one or more pharmaceutically acceptable excipients, and the preparation of such formulations will be readily understood by one of ordinary skill in the art.

EXAMPLES

Autoreactive T cells destroy pancreatic beta cells, yet therapies directed to eliminating or tolerizing such T cells have not yet been successful at reversing human T1D (7). One explanation of the rising incidence of T1D and autoimmunity in general is the "hygiene hypothesis", which suggests that insufficient microbiological stimulation of the innate immune system primes the adaptive immune system towards autoimmunity (8). It has previously been reported that nonobese diabetic (NOD) mice have defects in innate immune cells, including macrophages and dendritic cells, which play a key role in disease pathogenesis (9-11). In addition, evidence has been equivocal on the role for TLR4 in T1D pathogenesis in NOD mice, with no effect on T1D reported in one model but accelerated incidence of T1D in another model of NOD mice lacking TLR4(12,13). Applicant has used an agonistic monoclonal antibody to TLR-4/MD-2 (14-16) to reverse new onset diabetes in a high percentage of newly diabetic NOD mice. Successful treatment was associated with inability of T cells to further transfer the disease to naïve recipients. Specific stimulation of the innate immune system may therefore restore tolerance in the aberrant adaptive immune system and reverse new onset T1D, thus suggesting a new immunological approach to treatment of T1D in humans.

Applicant has used an agonistic antibody to mouse TLR4/MD-2 (UT18) and a control non-agonistic antibody to TLR4/MD-2 (UT15). UT18 can induce classic, persistent "endotoxin tolerance" and the effect persists for a longer time than LPS, due to antibody persistence. It was rigorously demonstrated that there was no contaminating LPS in these antibody preparations. Applicant tested UT18 in the NOD mouse model of T1D with the goal of restoring immune tolerance.

The antibodies used were derived in TLR4 knockout mice by immunization with recombinant TLR4 as previously published (21). Antibody binding sites were determined by competitive binding studies, and activity assessed by markers of TLR4 activation. UT18 (and a virtually identical agonist antibody, UT12) binds to a site including TLR4 and MD2, and mediates agonistic effects (21). UT15 binds to a different TLR4 and MD2 site, and shows no signaling (21). UT18 can induce classic, persistent "endotoxin tolerance" at the dose used in Applicant's T1D reversal studies, and the effect persisted for a much longer time than LPS, due to antibody persistence (22). UT12/18 had a therapeutic effect in murine asthma, suppressing the ability of DCs to expand antigen specific T cells (23). It was rigorously demonstrated that there was no contaminating LPS in these antibody preparations (22). These findings plus the above considerations led Applicant to test UT18 and UT15 antibodies in the NOD mouse model of T1D to determine if immune tolerance could be restored.

UT18, but not UT15, significantly prevented T1D in NOD mice. Applicant next treated clinical T1D. NOD mice were monitored closely for weight loss, polyuria and hypotonic urine, at which point BG was typically ~200 mg/dl. Mice were then treated with two intraperitoneal (i.p.) 5 µg doses of UT18 or UT15, one week apart. The UT15 treated mice rapidly (within three weeks) progressed to end stage diabetes (BG>600 mg/dL) confirming that this cohort had true clinical diabetes. UT18 mice showed reversal of elevated BG with subsequent weight gain. 18/20 UT 18 treated mice showed a clinical response ($p<0.0001$), and 14/20 UT18 mice showed permanent reversal of diabetes vs. 0/12 UT15 mice ($P<0.002$, Fischers exact test; log rank $p=<0.0001$). Applicant re-treated mice with UT18 after the initial treatment if their BG first fell below 200 mg/dl, then rose above it. Ten of the UT18 treated mice had to be re-treated. The average time until UT18 re-treatment was 52.7 days in UT18 treated mice versus an average time to full disease onset of 17.6 days in UT15 mice. Re-treatment with UT18, (not UT15) successfully reversed recurrent disease up to a BG of 453 mg/dl. Only one mouse had no initial response to UT18.

Figure 2A:
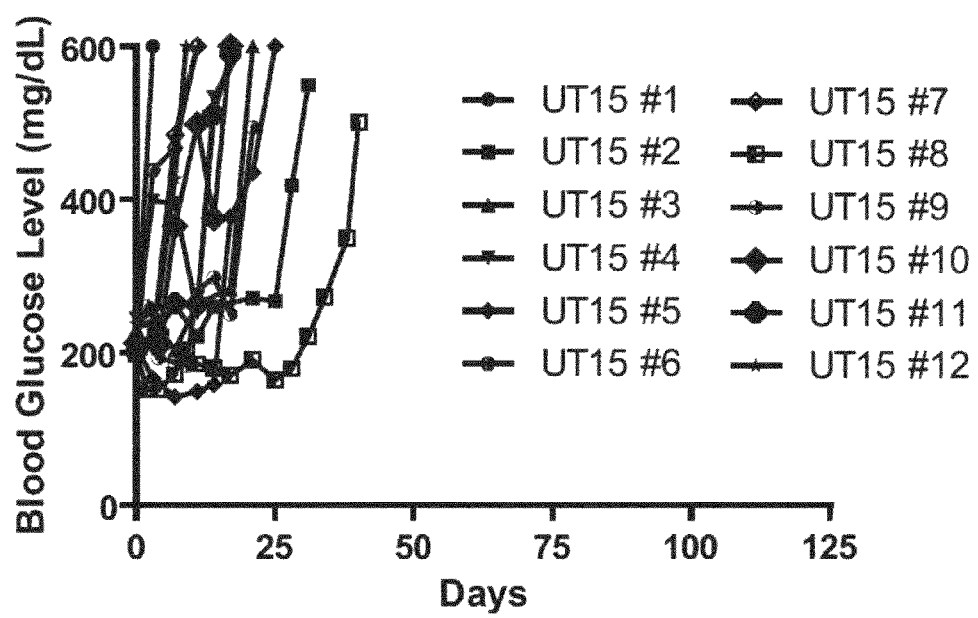
FIG. 2A-2G: UT18-Ab reverses new onset T1D.
Figure 2B:
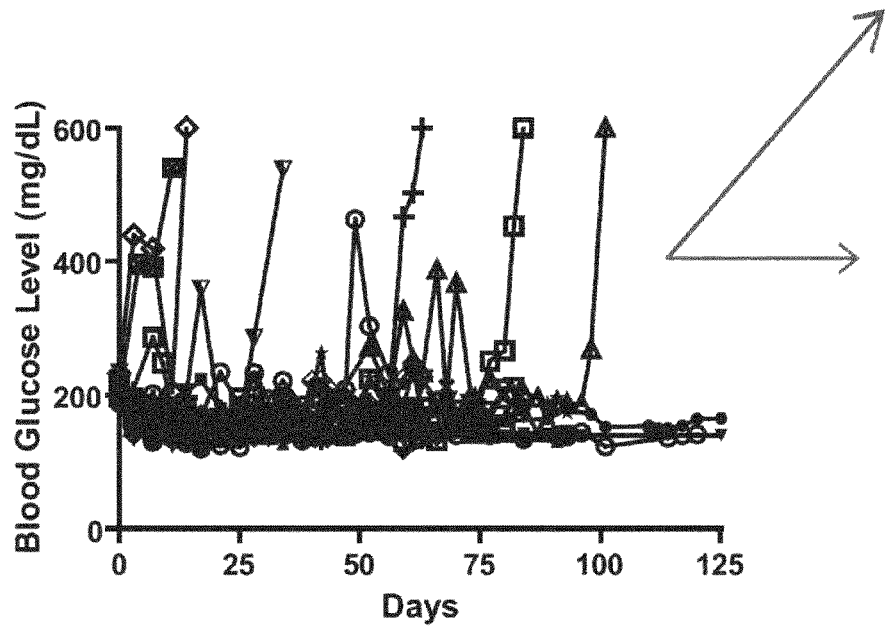
Figure 2C:
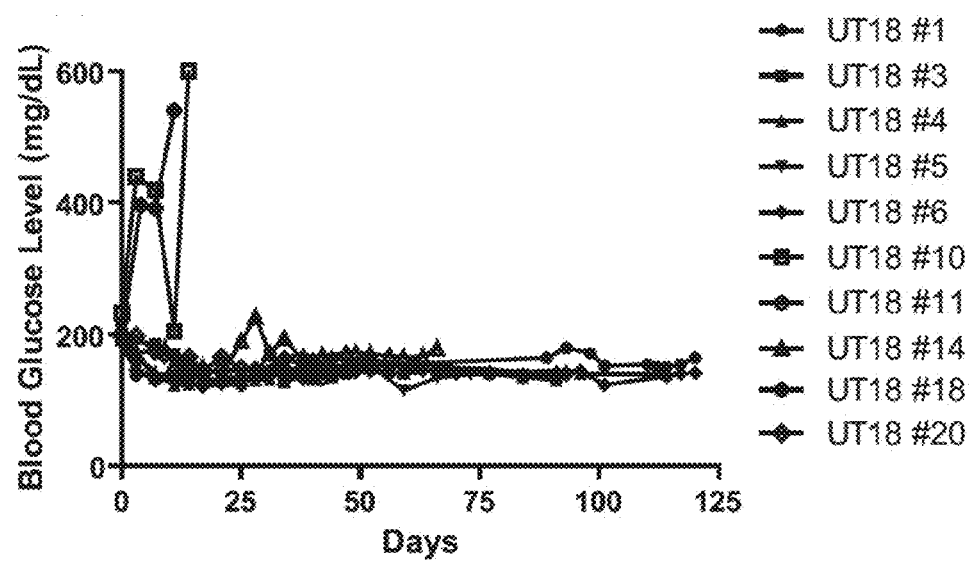
Figure 2D:
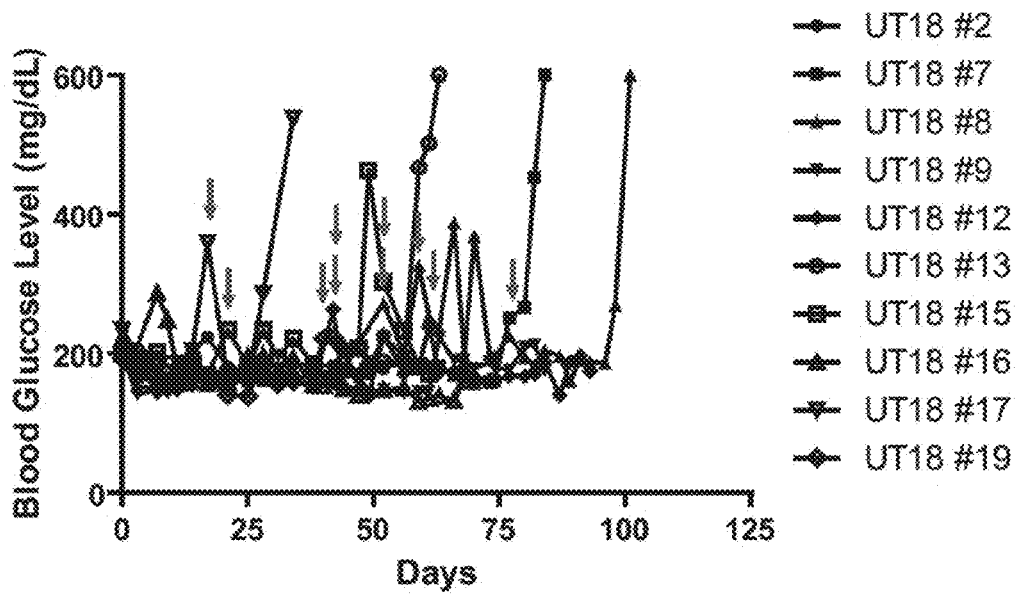
Figure 2E:
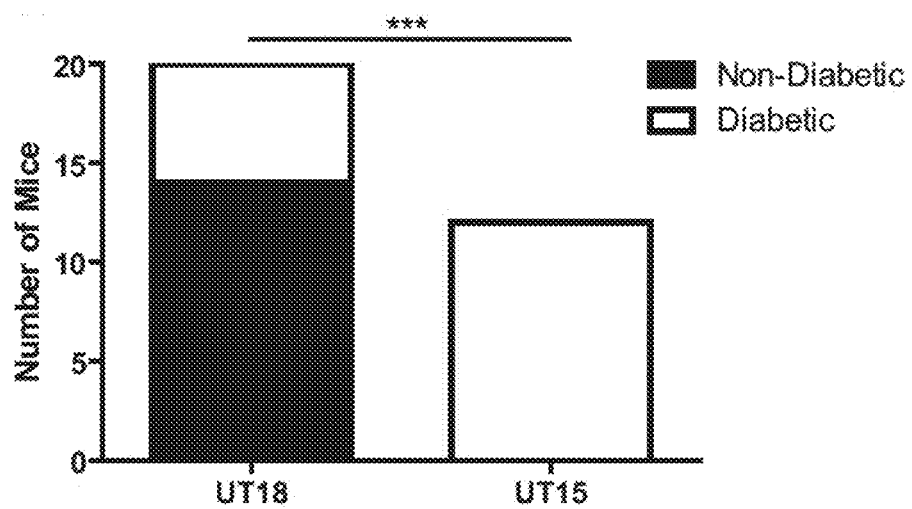
Figure 2F:
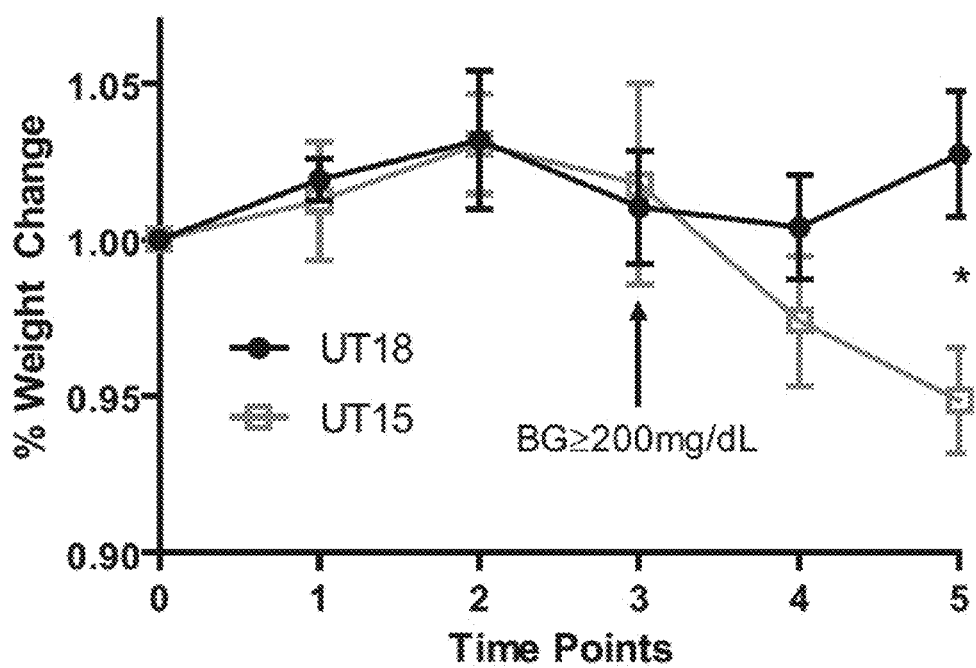

Using the agonistic antibody to mouse TLR4/MD-2 (UT18) and a control non-agonistic antibody to TLR4/MD2 (UT15), Applicant first showed that UT18 prevents T1D in NOD mice, and decreases insulitis, whereas UT15 and PBS treated groups were statistically indistinguishable and showed normal incidence of T1D (FIG. 1a, b, c). UT18, but not UT15, rapidly induced expansion and activation of macrophages, dendritic cells, and B cells, but had no effects on T cell numbers or proliferation (FIG. 1 d, e, f). Despite not directly activating T cells (FIG. 1g), however, UT18 treatment resulted in long-term expansion of the peripheral Treg population, consistent with the known regulation of adaptive cells by innate immunity (FIG. 1h)(17). To test whether UT18 could reverse new onset diabetes, Applicant aged NOD mice until the earliest clinical sign of T1D, polyuria. At this time, the average blood glucose (BG) was 208.7±16.22 mg/dL, (Table 1) and this stage just precedes onset of weight loss (FIG. 2d). Mice were then treated twice, one week apart, with either UT15 or UT18. UT15 treated mice rapidly (17.58±2.877 days) progressed to endstage T1D (BG>500, FIG. 2a). In striking contrast, a majority of UT18 treated mice (18/20 mice from 11 separate litters) had a clinical response to UT18 (FIG. 2 a, b, c, d). 10/20 UT18 treated mice received only the 2 initial treatments (FIG. 2c). Of those 10 mice, 8/10 had permanent reversal of T1D. 10/20 mice UT18 treated mice needed retreatment with UT18; they were re-treated whenever BG again exceeded 200 (FIG. 2c). 6/10 of these "re-treated" mice had persistent reversal of T1D, while 4/10 eventually progressed to endstage T1D. UT18 retreatment successfully reversed recurrent T1D up to a BG of 453 mg/dL (FIG. 2d), Thus 14/20 UT18 treated mice had permanent reversal of T1D compared to 0/12 UT15 treated mice (FIG. 2e) ($P<0.002$, Fischers exact test; log rank $p=<0.0001$). Successful treatment was associated with significantly decreased BG (from 205.1 to 160.8, $P=<0.0001$, Table one) and recovery of weight loss (FIG. 2f).

TABLE 1

UT18 AB treatment significantly improves blood glucose,
weight loss, and overall disease free time in newly diabetic NOD mice.
Values expressed as Mean ± SEM.

| | UnTx (n) | UT15 Ab (n) | UT18 Ab (n) | P value |
|---|---|---|---|---|
| Age of diabetes onset (days) | 177.4 ± 11.3 (12) | 166.8 ± 6.4 (12) | 183.5 ± 7.0 (21) | n.s. |
| Initial blood glucose (mg/dl) | 174.5 ± 9.2 (12) | 214.7 ± 4.5 (12) | 204.7 ± 3.4 (21) | n.s. |
| Final blood glucose (mg/dl) | 583.1 ± 7.7 (12) | 575.3 ± 11.4 (12) | 159.7 ± 5.5 (15) | P < 0.0001 |
| Days non-diabetic (non-diabetic TLR4-Ab) | 16.7 ± 3.2 (12) | 17.6 ± 2.9 (12) | 87.7 ± 8.8 (15) | P < 0.0001 |
| Days non-diabetic (diabetic TLR4-Ab) | 16.7 ± 3.2 (12) | 17.6 ± 2.9 (12) | 51.0 ± 15.3 (6) | P = 0.009 |

| | TLR4-Ab (initial) | TLR4-Ab (final) | |
|---|---|---|---|
| TLR4-Ab initial vs. final blood glucose (mg/dl) | 204.7 ± 3.4 (21) | 159.7 ± 5.5 (15) | P < 0.0001 |

Figure 2G:
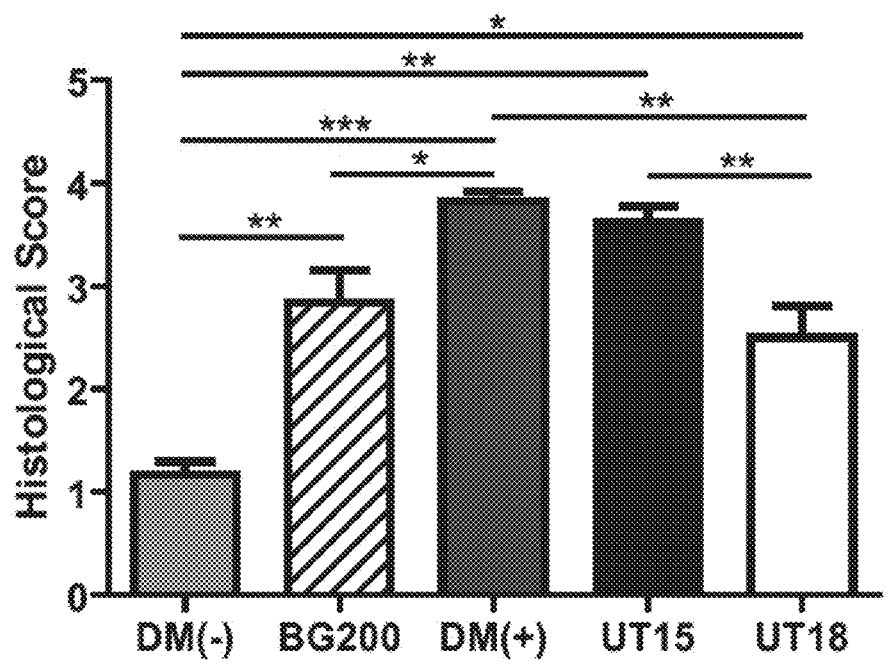
Figure 3A:
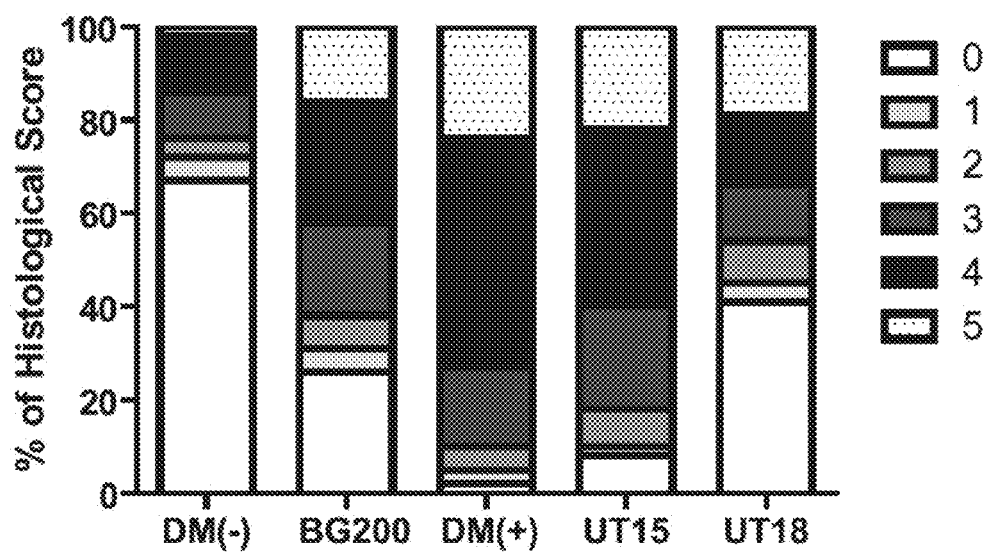
FIG. 3A-3E: UT18-Ab preserves insulin-positive pancreatic beta cells by reducing the percentage of severely infiltrated islets.

To understand the effects of UT18 on reversal of new onset diabetes, Applicant examined the histological effects of UT18 vs. UT15 treatment. Successful treatment with UT18 was associated with a significantly improved pancreatic islet histological score compared to UT15 (FIG. 2g, p=0.0083). To further understand these effects, Applicant quantified islet scores by severity in prediabetic mice, untreated endstage diabetic mice (BG>500 mg/dl), untreated new onset diabetic mice at the initial treatment point (BG>200 mg/dl), and UT15 vs. UT18 treated new onset diabetic mice (FIG. 3a). UT15 treated mice were no different than untreated endstage diabetic mice (FIG. 3a). Both the untreated BG200 mice and UT18 had fewer unaffected islets than prediabetic mice (FIG. 3a), Of great interest, however, UT18 treated mice showed a decrease in the number of severely infiltrated (stage 3 and 4) islets, and an increase in minimally affected islets (stages 0-2) compared to untreated new onset diabetic mice (FIG. 3a) suggesting that effective reversal of new onset diabetes was associated with increased numbers of protected pancreatic islets.

UT18 treated diabetic mice have decreased (but not absent) islet inflammation and preservation of insulin staining islet beta cells. The amount of insulin staining per islet was significantly increased in UT18 treated mice compared to 6 wk old non diabetic mice (DM(−)), but the total insulin area per slide and the insulin:glucagon ratio was not significantly different, since the young mice had more (but smaller) islets compared to UT18 treatment. Glucagon staining and total slide area was not significantly different in any of the groups (not shown). The finding of larger, but decreased total number of insulin staining islets suggests the preserved islets were hyperplastic as has been described in reversal of diabetes.

Figure 3B:
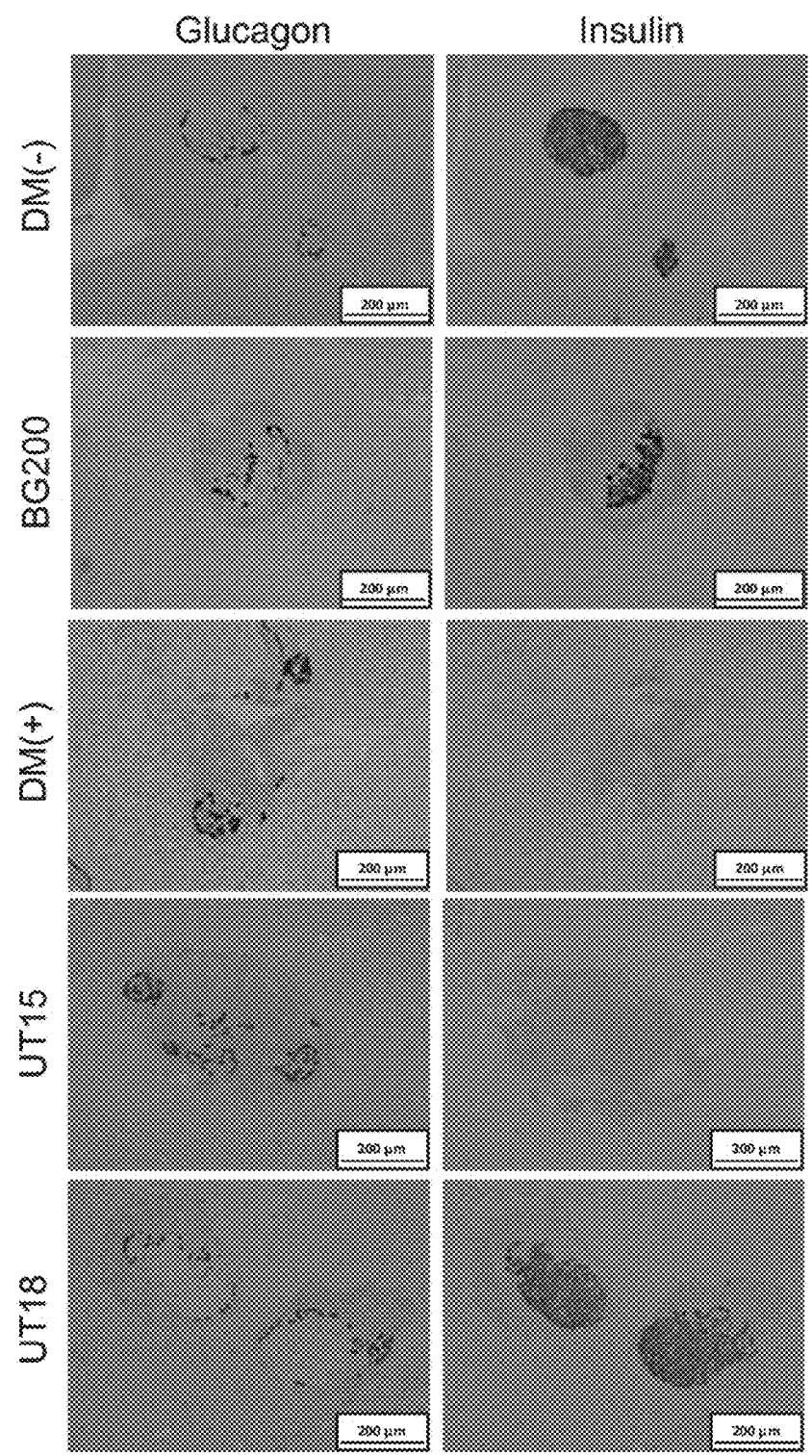
Figure 3C:
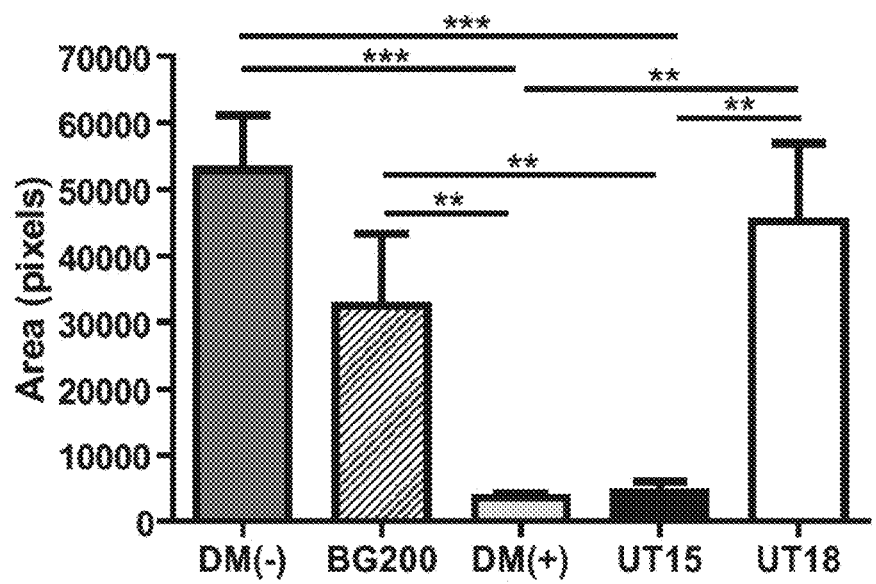
Figure 3D:
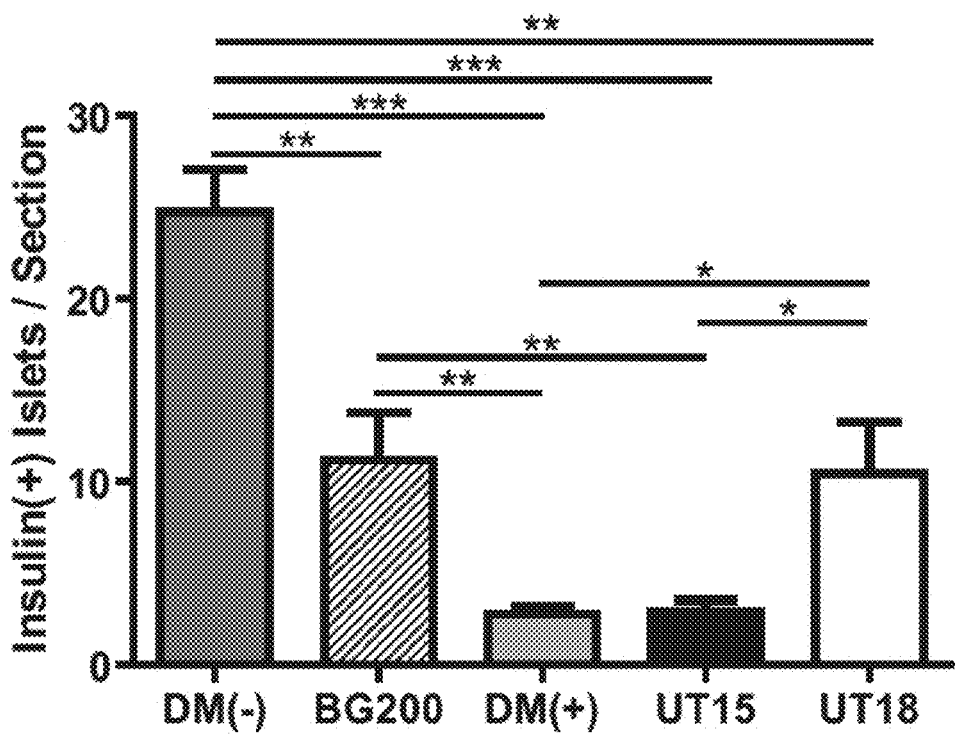
Figure 3E:
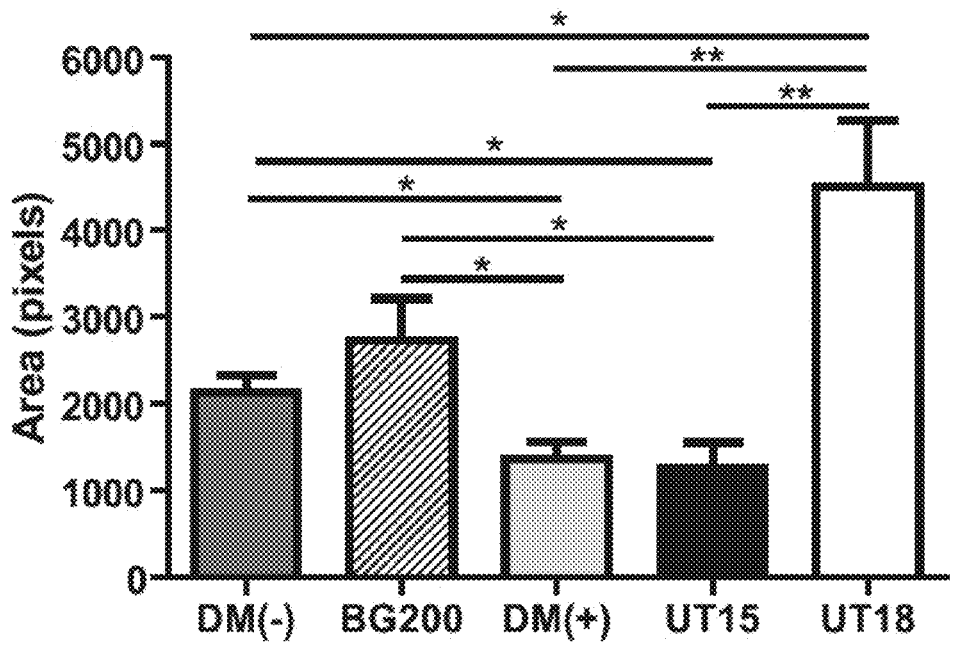

To further understand the islet biology in these five groups of mice, Applicant quantified the pancreatic beta cell insulin-positive area (18). As expected, prediabetic mice had the most total insulin staining and the most islets per section (FIG. 3b, c, d). The glucagon staining was not different between the groups (FIG. 3b and not shown). UT15 treated and endstage diabetic mice had minimal insulin staining area compared to prediabetic mice (FIGS. 3b and c), and a marked decrease in insulin positive islets (FIG. 3d). In contrast, UT18 treated mice had significantly greater insulin staining area than UT15, comparable to prediabetic mice (P=0.0035, FIGS. 3b and c), and to the untreated new onset diabetic mice. Both the untreated new onset diabetic mice and UT18 treated mice had similar numbers of insulin+ islets per section, significantly more than UT15 treated (FIG. 3d). Notably, however, UT18 mice had significantly larger islet insulin staining area, compared to both prediabetic mice and untreated new onset diabetic mice (FIG. 3e), suggestive of islet hyperplasia as has been previously reported in the setting of reversal of acute disease (19-21). The increased area of the UT18 treated islets compared to untreated BG200 mice is consistent with the improved histological score, and provides further evidence of a therapeutic effect of UT18 at the level of the pancreatic islet.

Figure 4A:
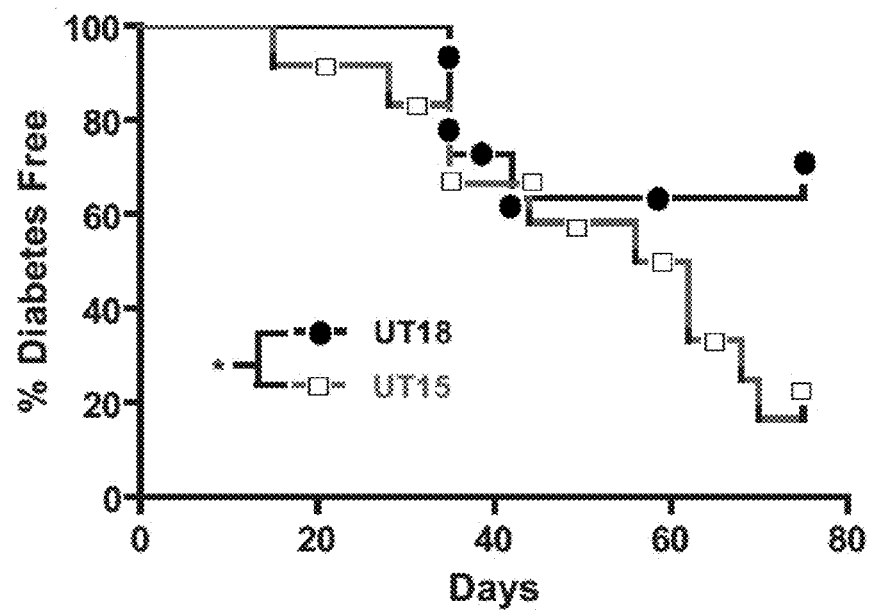
FIG. 4A-4C: Targeted UT18-Ab treatment of innate immune cells, in the absence of B or T cells, prevents T1D and increases downstream Treg numbers
Figure 4B:
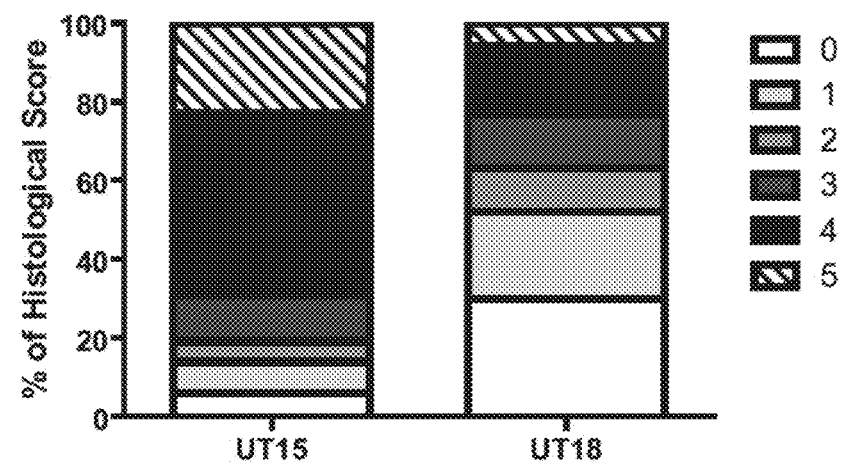
Figure 4B:
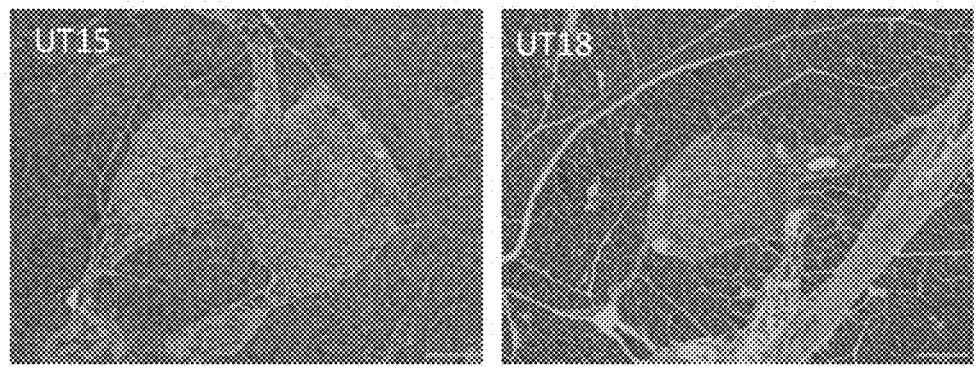
Figure 4C:
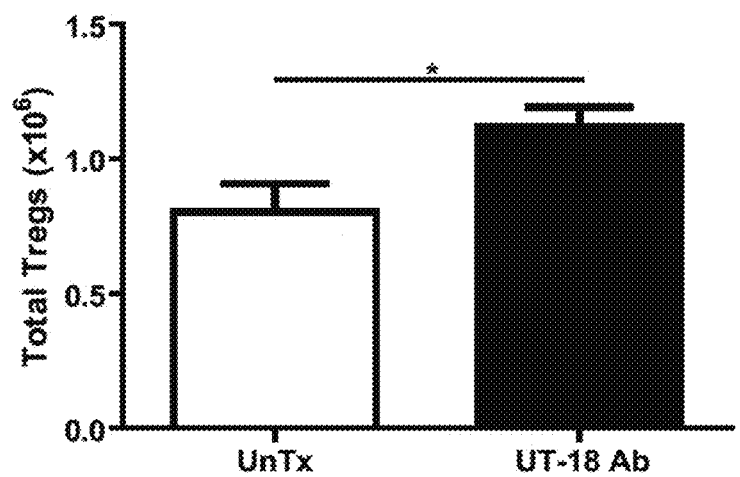
Figure 4C:
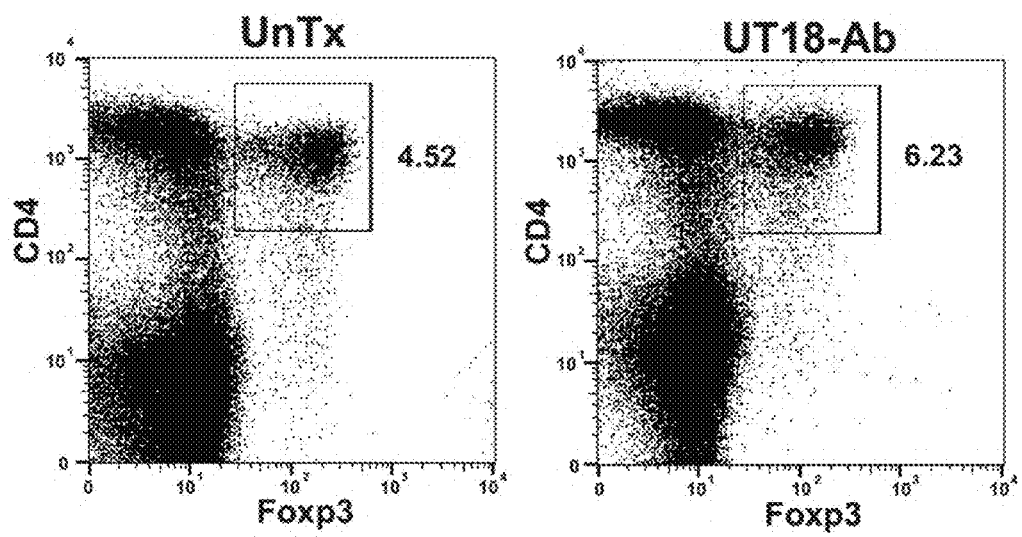

To begin to try to understand the immunological mechanism of these results, and given the result that there was an increase in Tregs after a single treatment of UT18 (FIG. 1h) while UT18 had no direct effect on T-cells alone (FIG. 1g), the Applicant tested whether the innate immune system could protect mice from transfer of T1D by CD4 and CD8 T cells. To test this Applicant treated female NOD.scid once a week for three weeks with either UT18 or UT15 starting at the 6 weeks of age and then transferred in pre-diabetic NOD CD4 and CD8 T cells. UT18 was able to significantly protect NOD.scid mice from developing disease compared to UT15 (p=0.046, FIG. 4a). This decrease in disease incidence correlated with a decrease in islet pathology (FIG. 4b). Moreover, the treatment of APCs alone, in the absence of T cells, Tregs, or B cells, led to a significant increase in the number of Treg cells in the NOD-scid recipient mice (FIG. 4c). These results strongly suggest that initial targeting of the innate immune system APCs produced a downstream upregulation of the critical Tregulatory subset, thus restoring tolerance and reversing acute T1D In summary, the data clearly shows that UT18 can reverse new onset diabetes. The initial cellular targets may be APCs, but the therapeutic effect is believed to ultimately involve a profound change in the adaptive immune system, possibly including both Treg and Teff substes. Without intending to be limited by theory, it is believe that the initial effect on innate immunity/APCs subsequently alters adaptive immunity.

These results show that under the right conditions, which are not yet fully understood, stimulation of innate immunity via TLR4/MD2, for example, using U18, can restore tolerance to the adaptive immune system that mediates destruction of pancreatic beta cells. This result is paradoxical compared to the current predominant paradigms of treating T1D. Autoimmune destruction of tissue is thought to be mediated by an overzealous adaptive immune response to self antigens. Treatment of autoimmunity has been directed to suppressing this over-zealous adaptive immune response;

e.g. in T1D much effort has attempted to tolerize or eliminate autoreactive T cells. In contrast, here we have activated innate immunity, yet this has had the downstream effect of suppressing the adaptive autoreactive response. Overall Applicant's results suggest the prospect of entirely new pathways of innate immune manipulation to restore adaptive immune tolerance in active T1D. The mechanisms of this strong clinical effect should therefore be pursued in depth. Since one agonistic anti-TLR4 agent is already FDA approved (22, 23), and more are under development 24, it will be possible to test this approach in new onset human diabetics.

REFERENCES

1 Gale, E. A. The rise of childhood type 1 diabetes in the 20th century. Diabetes 51, 3353-3361 (2002).
2 Gardner, S. G., Bingley, P. J., Sawtell, P. A., Weeks, S. & Gale, E. A. Rising incidence of insulin dependent diabetes in children aged under 5 years in the Oxford region: time trend analysis. The Bart's-Oxford Study Group. BMJ 315, 713-717 (1997).
3 Long, A. E., Gillespie, K. M., Rokni, S., Bingley, P. J. & Williams, A. J. Rising incidence of type 1 diabetes is associated with altered immunophenotype at diagnosis. Diabetes 61, 683-686, doi:db11-0962 [pii] 10.2337/db11-0962 (2012).
4 Onkamo, P., Vaananen, S., Karvonen, M. & Tuomilehto, J. Worldwide increase in incidence of Type I diabetes—the analysis of the data on published incidence trends. Diabetologia 42, 1395-1403, doi:10.1007/s001250051309 (1999).
5 Patterson, C. C., Dahlquist, G. G., Gyurus, E., Green, A. & Soltesz, G. Incidence trends for childhood type 1 diabetes in Europe during 1989-2003 and predicted new cases 2005-20: a multicentre prospective registration study. Lancet 373, 2027-2033, doi:S0140-6736(09)60568-7 [pii] 10.1016/S0140-6736(09)60568-7 (2009).
6 Atkinson, M. A., Eisenbarth, G. S. & Michels, A. W. Type 1 diabetes. Lancet 383, 69-82, doi:S0140-6736(13)60591-7 [pii] 10.1016/S0140-6736(13)60591-7 (2014).
7 Culina, S., Boitard, C. & Mallone, R. Antigen-based immune therapeutics for type 1 diabetes: magic bullets or ordinary blanks? Clin Dev Immunol 2011, 286248, doi:10.1155/2011/286248 (2011).
8 Bach, J. F. & Chatenoud, L. The hygiene hypothesis: an explanation for the increased frequency of insulin-dependent diabetes. Cold Spring Harb Perspect Med 2, a007799, doi:10.1101/cshperspect.a007799 a007799 [pii] (2012).
9 Nikolic, T., Geutskens, S. B., van Rooijen, N., Drexhage, H. A. & Leenen, P. J. Dendritic cells and macrophages are essential for the retention of lymphocytes in (peri)-insulitis of the nonobese diabetic mouse: a phagocyte depletion study. Lab Invest 85, 487-501, doi:3700238 [pii] 10.1038/labinvest.3700238 (2005).
10 Serreze, D. V., Gaedeke, J. W. & Leiter, E. H. Hematopoietic stem-cell defects underlying abnormal macrophage development and maturation in NOD/Lt mice: defective regulation of cytokine receptors and protein kinase C. Proc Natl Acad Sci USA 90, 9625-9629 (1993).
11 Weaver, D. J., Jr. et al. Dendritic cells from nonobese diabetic mice exhibit a defect in NF-kappa B regulation due to a hyperactive I kappa B kinase. J Immunol 167, 1461-1468 (2001).
12 Gulden, E. et al. Toll-like receptor 4 deficiency accelerates the development of insulin-deficient diabetes in non-obese diabetic mice. PLoS One 8, e75385, doi:10.1371/journal.pone.0075385 (2013).
13 Dong, B. et al. TLR4 regulates cardiac lipid accumulation and diabetic heart disease in the nonobese diabetic mouse model of type 1 diabetes. Am J Physiol Heart Circ Physiol 303, H732-742, doi:10.1152/ajpheart.00948.2011 (2012).
14 Bahrun, U. et al. Preparation and characterization of agonistic monoclonal antibodies against Toll-like receptor 4-MD-2 complex. Hybridoma (Larchmt) 26, 393-399, doi:10.1089/hyb.2007.0523 (2007).
15 Matsushita, H. et al. Endotoxin tolerance attenuates airway allergic inflammation in model mice by suppression of the T-cell stimulatory effect of dendritic cells. Int Immunol 22, 739-747, doi:dxq062 [pii] 10.1093/intimm/dxq062 (2010).
16 Ohta, S. et al. Induction of long-term lipopolysaccharide tolerance by an agonistic monoclonal antibody to the toll-like receptor 4/MD-2 complex. Clin Vaccine Immunol 13, 1131-1136, doi:13/10/1131 [pii] 10.1128/CVI.00173-06 (2006).
17 Bour-Jordan, H. et al. Costimulation controls diabetes by altering the balance of pathogenic and regulatory T cells. J Clin Invest 114, 979-987, doi:10.1172/JCI20483 (2004).
18 Sreenan, S. et al. Increased beta-cell proliferation and reduced mass before diabetes onset in the nonobese diabetic mouse. Diabetes 48, 989-996 (1999).
19 Chong, A. S. et al. Reversal of diabetes in non-obese diabetic mice without spleen cell-derived beta cell regeneration. Science 311, 1774-1775, doi:311/5768/1774 [pii] 10.1126/science.1123510 (2006).
20 Nishio, J. et al. Islet recovery and reversal of murine type 1 diabetes in the absence of any infused spleen cell contribution. Science 311, 1775-1778, doi:311/5768/1775 [pii] 10.1126/science.1124004 (2006).
21 Okubo, Y. et al. Hyperplastic islets observed in "reversed" NOD mice treated without hematopoietic cells. Diabetes Res Clin Pract 79, 18-23, doi:S0168-8227(07)00428-7 [pii] 10.1016/j.diabres.2007.08.020 (2008).
22 Michaud, J. P. et al. Toll-like receptor 4 stimulation with the detoxified ligand monophosphoryl lipid A improves Alzheimer's disease-related pathology. Proc Natl Acad Sci USA 110, 1941-1946, doi:1215165110 [pii] 10.1073/pnas.1215165110 (2013).
23 Madonna, G. S., Peterson, J. E., Ribi, E. E. & Vogel, S. N. Early-phase endotoxin tolerance: induction by a detoxified lipid A derivative, monophosphoryl lipid A. Infect Immun 52, 6-11 (1986).
24 Vacchelli, E. et al. Trial watch: FDA-approved Toll-like receptor agonists for cancer therapy. Oncoimmunology 1, 894-907, doi:10.4161/onci.20931 2012ONCOIMM0177 [pii] (2012).

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating Type I diabetes in a subject, comprising the step of administering a TLR4/MD-2 specific antibody or an antigen-binding fragment thereof.

2. The method of claim 1, wherein said Type I diabetes is new onset diabetes.

3. The method of claim 1, wherein said antibody is a monoclonal antibody.

4. The method of claim 1 wherein said TLR4/MD-2 antibody is administered in an amount sufficient to improve blood glucose in said subject, decrease islet cell inflammation, or combinations thereof.

* * * * *

UNITED STATES PATENT AND TRADEMARK OFFICE
CERTIFICATE OF CORRECTION

PATENT NO. : 9,938,348 B2
APPLICATION NO. : 15/302772
DATED : April 10, 2018
INVENTOR(S) : William Ridgway Page 1 of 1

It is certified that error appears in the above-identified patent and that said Letters Patent is hereby corrected as shown below:

In the Claims

Column 12, Claim 1, Lines 10-11 reads:
"...TLR4/MD-2 specific antibody..." which should be deleted and replaced with "...TLR4/MD-2 specific agonistic antibody..."

Signed and Sealed this
Fifth Day of June, 2018

Andrei Iancu
*Director of the United States Patent and Trademark Office*